US00PP29502P3

(12) United States Plant Patent
Bronsther

(10) Patent No.: US PP29,502 P3
(45) Date of Patent: Jul. 17, 2018

(54) ***CHAMAECYPARIS* 'RIKACPMC'**

(50) Latin Name: *Chamaecyparis pisifera*
Varietal Denomination: RIKACPMC

(71) Applicant: Rika Bronsther, Hemstead, NY (US)

(72) Inventor: Rika Bronsther, Hemstead, NY (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 15/530,102

(22) Filed: Dec. 1, 2016

(65) Prior Publication Data

US 2018/0160592 P1 Jun. 7, 2018

(51) Int. Cl.
*A01H 5/02* (2018.01)

(52) U.S. Cl.
USPC ..... Plt./213

(58) Field of Classification Search
USPC ..... Plt./213
See application file for complete search history.

(56) References Cited

PUBLICATIONS https://www.soonerplantfarm.com/index.cfm/fuseaction/plants.main/typeID/162/listPage/2/show/all/index.htm Jan. 29, 2013.*
https://www.soonerplantfarm.com/index.cfm?fuseaction=plants.printkwSearch&variety=Chamaecyparis Jun. 27, 2009.*

* cited by examiner

*Primary Examiner* — Annette H Para
(74) *Attorney, Agent, or Firm* — Cassandra Bright

(57) ABSTRACT

A new and distinct *Chamaecyparis* cultivar named 'RIKACPMC' is disclosed, characterized by distinctive upright and semi-pyramidal plant form, lime yellow foliage maintained throughout Winter. The new cultivar is a *Chamaecyparis*, suitable for ornamental garden purposes.

2 Drawing Sheets

Latin name of the genus and species: *Chamaecyparis pisifera.*

Variety denomination: 'RIKACPMC'.

BACKGROUND OF THE INVENTION

The new cultivar is a product of chance discovery by the inventor, Rika Bronsther. This new variety, hereinafter referred to as 'RIKACPMC', was selected as a naturally occurring branch mutation from an unnamed, unpatented *Chamaecyparis pisifera*. The novel variety was discovered in a garden in Hemstead, N.Y. during 2005.

After identifying the new variety as a potentially interesting selection, first propagation of 'RIKACPMC' occurred by semi-hardwood cuttings at a commercial nursery in Grand Haven, Mich. April 2005. The inventor continued controlled testing and propagation, assessing stability of the unique characteristics of this variety. Five generations have been reproduced and have shown that the unique features of this cultivar are stable and reproduced true to type.

SUMMARY OF THE INVENTION

The cultivar 'RIKACPMC' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'RIKACPMC' These characteristics in combination distinguish 'RIKACPMC' as a new and distinct *Chamaecyparis* cultivar:

1. Upright and semi-pyramidal growth habit.
2. Bright lime yellow foliage.
3. Foliage color well maintained during the Winter.

COMPARISON TO PARENT VARIETY

'RIKACPMC' is similar in most horticultural characteristics to the parent variety. Foliage of the new cultivar 'RIKACPMC' however, is distinctively lime green, whereas the parent variety has medium green foliage.

COMMERCIAL COMPARISON

In addition to the seed parent, 'RIKACPMC' can be compared to the commercial variety *Chamaecyparis pisifera* 'Golden Mop', unpatented. The varieties are similar in most horticultural characteristics, however, plants of 'RIKACPMC' are taller and grow faster. Foliage of the new variety maintains its lime-yellow hue throughout the year. The comparator has yellow new growth, turning more green in the Summer. Foliage of the new variety is planar, foliage of this comparator is threadlike.

'RIKACPMC' can be compared to the commercial variety *Chamaecyparis pisifera* 'Kost Yellow', unpatented. The varieties are similar in most horticultural characteristics, however, plants of 'RIKACPMC' have a semi-pyramidal form, whereas this comparator has a weeping and mounding form. Plants of the new variety are taller than plants of 'Kost Yellow'.

BRIEF DESCRIPTION OF THE PHOTOGRAPHS

Figure 1:
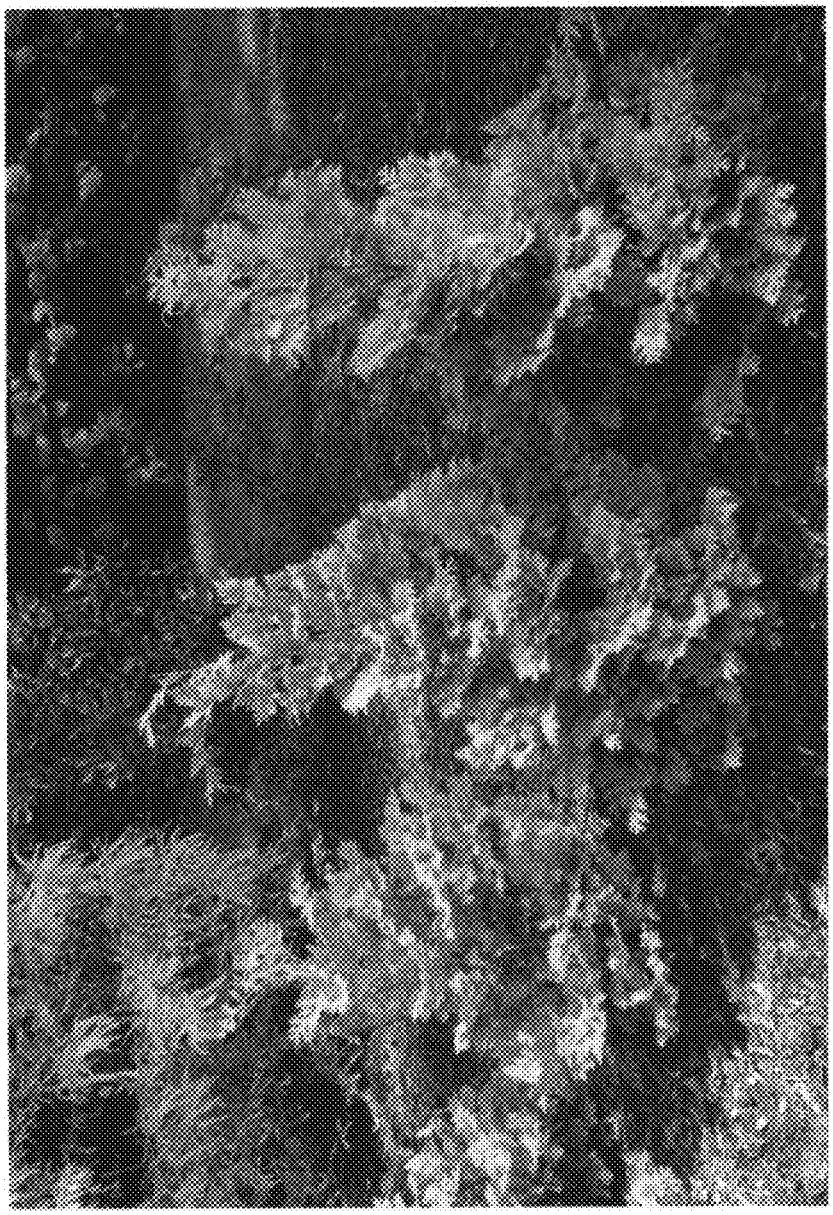

The accompanying photograph in FIG. 1 illustrates in full color a typical plants of 'RIKACPMC' grown outdoors in Grand Haven, Mich. Plants in FIG. 1 are approximately 5 years old, and exhibit the characteristic semi-pyramidal growth.

Figure 2:
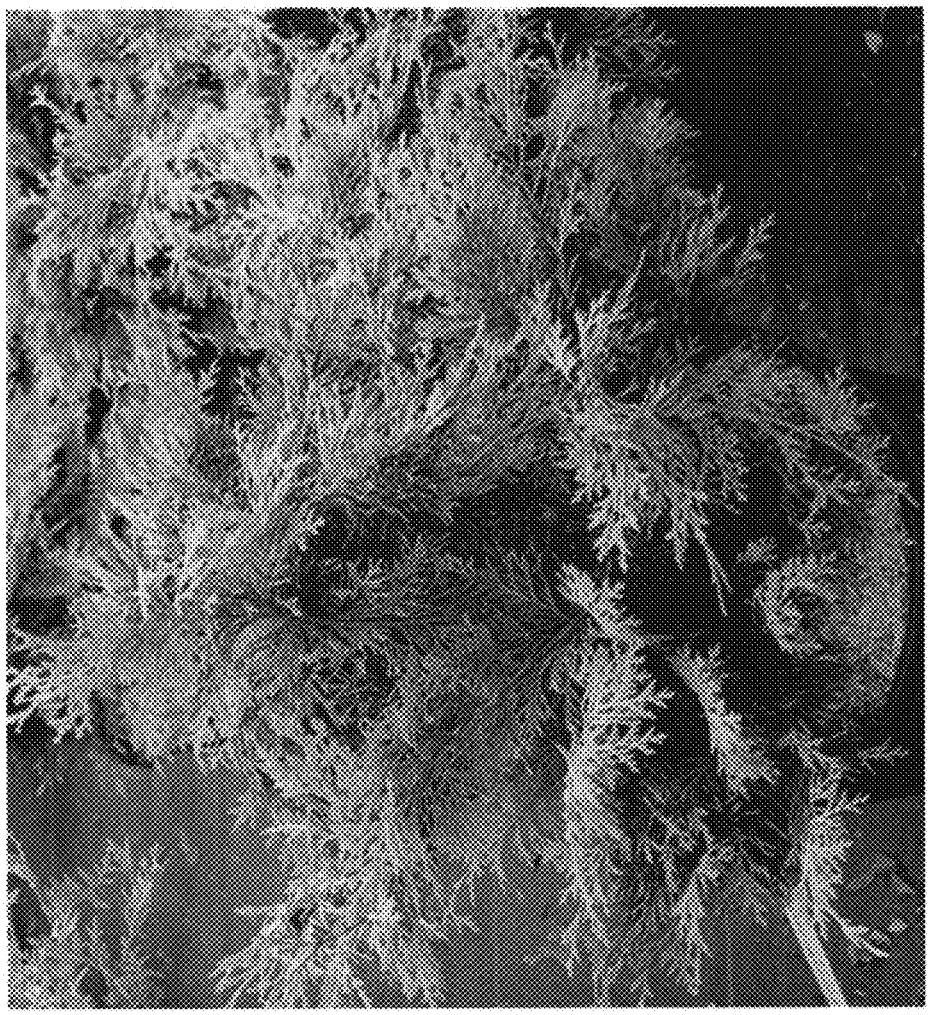

FIG. 2 illustrates a plant of the new variety at approximately 2 years old in a 2 gallon container.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'SMNBDO' plants grown in a poly greenhouse during Summer, in Grand Haven, Mich. USA. The growing temperature ranged from 18° C. to 27° C. during the day and from 5° C. to 10° C. during the night. General light conditions are natural sunlight. Measurements and numerical values represent averages of typical plant types.

Botanical classification: *Chamaecyparis pisifera* 'RIKACPMC'.

PROPAGATION

Typical method: Softwood cuttings.

Time to initiate rooting: 120 days at approximately 10° C.

Time to produce a rooted young plant: 180 days at approximately 10° C. to 13° C.

Root description: Fibrous, both fine and fleshy roots present. Moderately well branched. Colored light brown, not accurately measured with an R.H.S. chart.

PLANT

Age of plant described: Between 2 and 3 years.

Container size of plant described: 2 gallon.

Growth habit: Upright, semi-pyramidal evergreen tree. Slightly mounding in juvenility, upright with maturity.

Height: Approximately 53 cm in a 2 gallon pot.

Plant spread: Approximately 39 cm in a 2 gallon pot.

Typical growth rate: Moderate.

Pinching required: Not necessary, but, commercially can be trimmed when young to promote more branching.

Branching characteristics: Lateral branching occurring from base through top of plant.

Angle: Occurring at angles of approximately 20 to 30° from stem.

Quantity of lateral branches: Typical range 15 to 22.

Length of lateral branches: Average range 9 to 15 cm.

Diameter of lateral branches: 5 mm.

Lateral branch shape in cross section: Round.

Lateral branch strength: Very strong.

Lateral branch color: Grey-Brown 199C.

Lateral branch texture: Rough with overlapping scales.

Internode length: Average range between 1.0 to 1.5 cm.

FOLIAGE

General description: Overlapping scales.

Leaf:

*Arrangement*.—Alternate.

*Shape of blade*.—Scale-like.

*Average length*.—Approximately 2.25 to 2.5 mm.

*Average width*.—Approximately 2.5 mm.

*Apex*.—Apiculate.

*Base*.—Cuneate.

*Attachment*.—Sessile.

*Margin*.—Entire.

*Texture of top surface*.—Smooth, moderately glossy.

*Texture of bottom surface*.—Smooth, moderately glossy.

*Leaf internode length*.—Overlapping.

*Foliage color*.—Upper Section of Branchlet: Young foliage upper side: Yellow 8A. Young foliage under side: Yellow 8A, about 50% covered with overlay Yellow-Green 144A. Mid-Section of Branchlet: Young foliage upper side: Yellow-Green 144A, with slight speckling Greyed-Green 197A. Apex Yellow 8A. Young foliage under side: Yellow-Green 144A with complete overlay 197A. Lower Section of Branchlet: Mature foliage upper side: Yellow-Green 144A, with slight speckling Greyed-Green 197A. Mature foliage under side: Yellow-Green 144A with complete overlay 197A.

*Venation*.—Linear, indistinguishable from leaf blade.

*Durability of foliage to stresses*.—Flexible and resistant to breakage.

*Fragrance*.—Very mild cedar scent.

FLOWER

Flowering not observed.

OTHER CHARACTERISTICS

Disease and pest resistance: Neither resistance nor susceptibility observed.

Drought tolerance: No tolerance for drought.

Temperature tolerance: USDA Zones 4 through 8.

What is claimed is:

1. A new and distinct cultivar of *Chamaecyparis* plant named 'RIKACPMC' as herein illustrated and described.

* * * * *